US00PP09374P

United States Patent [19]

Zary

[11] Patent Number: Plant 9,374

[45] Date of Patent: Nov. 21, 1995

[54] SHRUB ROSE PLANT NAMED 'JACWADE'

[75] Inventor: Keith W. Zary, Thousand Oaks, Calif.

[73] Assignee: Bear Creek Gardens, Inc., Medford, Oreg.

[21] Appl. No.: 335,635

[22] Filed: Nov. 8, 1994

[51] Int. Cl.[6] ..... A01H 5/00

[52] U.S. Cl. ..... Plt./1

[58] Field of Search ..... Plt./1, 8.1

[56] References Cited

U.S. PATENT DOCUMENTS

P.P. 8,719 5/1994 Zary ..... Plt./1

*Primary Examiner*—Howard J. Locker

*Attorney, Agent, or Firm*—Klarquist Sparkman Campbell Leigh & Whinston

[57] ABSTRACT

A shrub rose plant having dwarf, low growing habit of growth; small, white recurrent blooms; dark green, glossy, disease-resistant foliage; ease of propagation from softwood cuttings; and manyg lands on the peduncles.

1 Drawing Sheet

The present invention relates to a new and distinct variety of rose plant of the shrub class which was originated by me by crossing the unpatented variety KORimro with the variety MACminmo, U.S. Plant Pat. No. 7,319.

The primary objective of this breeding was to produce a new rose variety having the low growing habit and disease resistance of the once blooming female parent, combined with the recurrent flowering of the male parent. The objective was substantially achieved, along with other desirable improvements, as evidenced by the following unique combination of characteristics that are outstanding in the new variety and that distinguish it from its parents, as well as from all other varieties of which I am aware:

1. Dwarf, low growing habit of growth;
2. Small, white recurrent blooms;
3. Dark green, glossy, disease-resistant foliage;
4. Ease of propagation from softwood cuttings; and
5. Presence of many glands on the peduncles.

Asexual reproduction of this new variety by softwood cutting, as performed at Wasco, Calif., shows that the foregoing characteristics and all other features come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORimro (unpatented).

*Pollen parent.*—MACminmo, U.S. Plant Pat. No. 7,319.

Classification:

*Botanical.*—*Rosa hybrida.*

*Commercial.*—Shrub.

FLOWER

Observations made from specimens grown in a garden environment at Somis, Calif. from April to September, 1994.

Blooming habit: Recurrent.

Bud:

*Size.*—½ inch long when the petals start to unfurl.

*Form.*—The bud form is short, pointed ovoid.

*Color.*—When sepals first divide, bud color is White Group 155D. When half blown, the upper sides of the petals are White Group 155D; and the lower sides of the petals are White Group 155D.

*Sepals.*—Color: Green Group 138B. Surface texture: Covered in fine hairs. There are three lightly appendaged speals. There are two unappendaged sepals with hairy edges.

*Receptacle.*—Color: Green Group 137C, but often with a bronze cast when exposed to full sun. Shape: Funnel. Size: Small (3/16 inch×3/16 inch). Surface: Smooth.

*Peduncle.*—Length: Short (½ inch). Surface: Glandular. Color: Medium green and bronzy when exposed to full sun. Strength: Stiff, erect, slender.

Bloom:

*Size.*—Small. Average open size is 1 to 1¼ inches.

*Borne.*—Singly and several together in cluster of 3 to 7 flowers. If in clusters: Pyramidal.

*Stems.*—Short. Average length is about 5 to 6 inches.

*Form.*—When first open: High centered. Permanence: Flattens, outer petals curl back.

*Petalage.*—Number of petals under normal conditions: 45 to 50.

*Color.*—The upper side of the petals is White Group 155D. The reverse side of the petals is White Group 155D. At the base of each petal is a small yellow half moon (⅛ inch×⅛ inch) at the point of attachment. The major color on the upper side is White Group 155D.

*Variegations.*—Occasional greenish streak on the guard petals.

*Discoloration.*—No change in the general tonality at the end of the first day, nor at the end of the third day.

*Fragrance.*—Slight.

Petals:

*Texture.*—Thin.

*Shape.*—Deltoid.

*Form.*—Tips slightly recurved.

*Arrangement.*—Imbricated, with many petaloids in the center.

*Persistence.*—Drop off cleanly.

*Lastingness.*—On the plant: Short (4 days). As a cut flower: Not tested.

Reproductive parts:

*Anthers.*—Size: Small. Quantity: Few. Color: Yellow. Arrangement: Regular around styles, mixed with petaloids.

*Filaments.*—Color: White.

*Pollen.*—Color: Lemon yellow.

*Styles.*—Color: Greenish white.

*Stigmas.*—Color: Greenish white.

Form: Shrub.

Growth: Vigorous, dwarf, sprawling; California height after one year of growth is 14 to 18 inches with a spread of 20 to 24 inches.

Foliage:

*Number of leaflets on normal mid-stem leaves.*—5.

*Size.*—Small.

*Quantity.*—Abundant.

*Color.*—New foliage: Dark glossy green. Old foliage: Dark glossy green. Upper side Green Group 139A and lower side Green Group 137C.

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Smooth with occasional prickles.

*Stipules.*—Medium, serrated, bearded.

Disease resistance.—Resistant to mildew and rust under normal growing conditions at Somis, Calif.

Wood:

*New wood.*—Color: Reddish green. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked downward.

*Color when young.*—Red.

Small prickles:

*Quantity.*—On main stalks: None. On laterals: None.

I claim:

1. A new and distinct variety of rose plant of the shrub class, substantially as herein shown and described, characterized particularly as to novelty by the unique combination of its dwarf, low growing habit of growth; small, white recurrent blooms; dark green, glossy, disease-resistant foliage; ease of propagation from softwood cuttings; and presence of many glands on the peduncles.

* * * * *

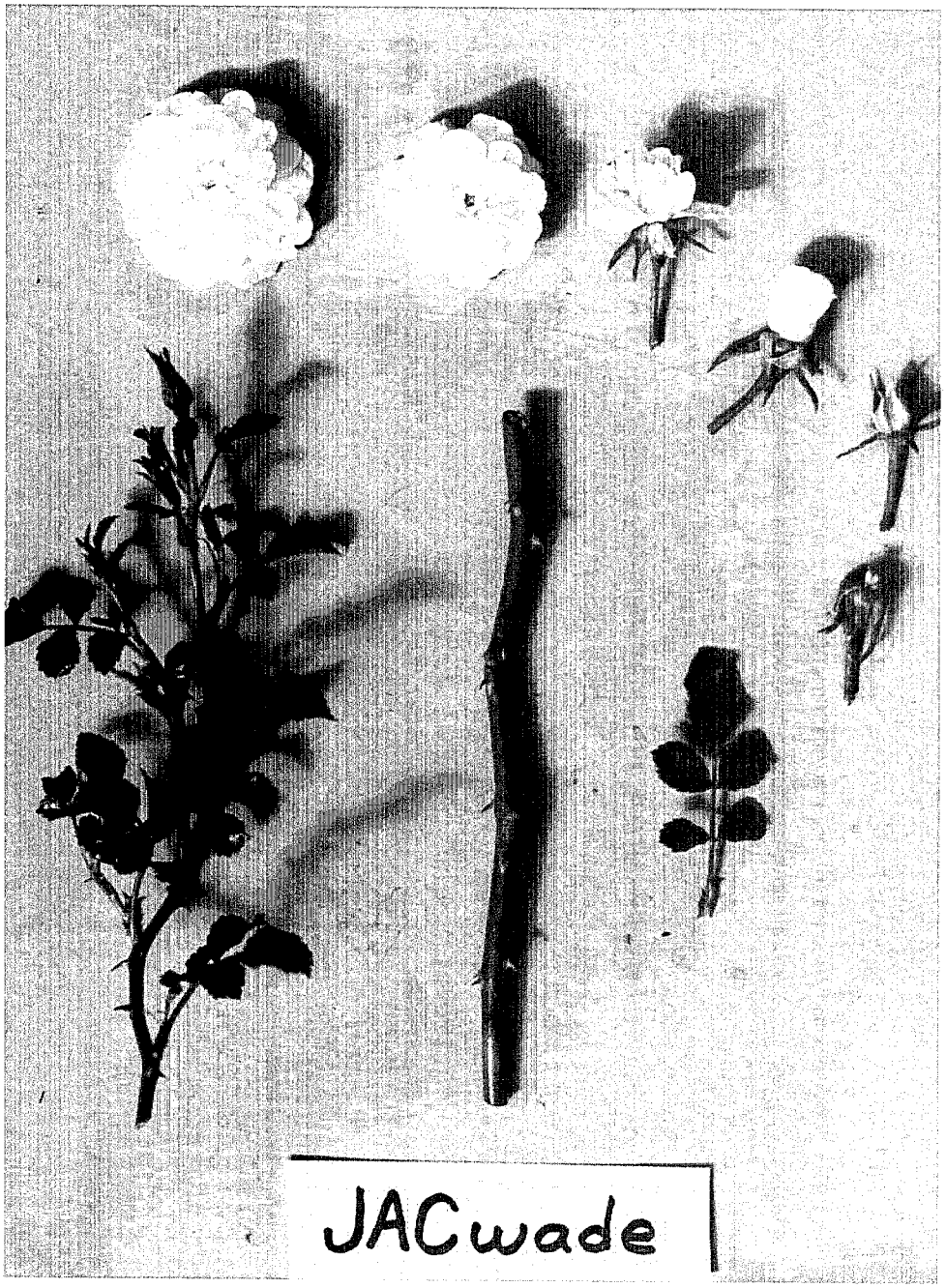
JACwade